(12) United States Patent
Uchiyama et al.

(10) Patent No.: US 7,964,545 B2
(45) Date of Patent: Jun. 21, 2011

(54) SKIN CLEANSING COMPOSITION

(75) Inventors: Tomoko Uchiyama, Wakayama (JP); Hayato Yoshikawa, Wakayama (JP)

(73) Assignee: Kao Corporation, Tokyo (JP)

( * ) Notice: Subject to any disclaimer, the term of this patent is extended or adjusted under 35 U.S.C. 154(b) by 175 days.

(21) Appl. No.: 12/307,382

(22) PCT Filed: Jul. 3, 2007

(86) PCT No.: PCT/JP2007/000726
§ 371 (c)(1),
(2), (4) Date: Jan. 5, 2009

(87) PCT Pub. No.: WO2008/004343
PCT Pub. Date: Jan. 10, 2008

(65) Prior Publication Data
US 2009/0286707 A1    Nov. 19, 2009

(30) Foreign Application Priority Data

Jul. 4, 2006    (JP) .................................. 2006-184820

(51) Int. Cl.
*A61K 7/50* (2006.01)
(52) U.S. Cl. ........ 510/130; 510/136; 510/159; 510/424; 510/437; 510/480; 510/499; 424/70.1
(58) Field of Classification Search .................. None
See application file for complete search history.

(56) References Cited

U.S. PATENT DOCUMENTS

| 5,866,110 | A | 2/1999 | Moore et al. |
| 2006/0116305 | A1 | 6/2006 | Yamato et al. |
| 2006/0160714 | A1* | 7/2006 | Terada .......................... 510/119 |

FOREIGN PATENT DOCUMENTS

| JP | 10 306298 | 11/1998 |
| JP | 2001 172671 | 6/2001 |
| JP | 2003-212733 | 7/2003 |
| JP | 2004 2632 | 1/2004 |
| JP | 2004-91522 | 3/2004 |
| JP | 2004-168951 | 6/2004 |
| JP | 2006 28217 | 2/2006 |
| JP | 2006 265547 | 10/2006 |
| JP | 2006 342225 | 12/2006 |
| JP | 2007 55997 | 3/2007 |
| JP | 2007 197420 | 8/2007 |
| WO | 2004 098549 | 11/2004 |
| WO | 2007 077668 | 7/2007 |

OTHER PUBLICATIONS

U.S. Appl. No. 12/306,006, filed Dec. 22, 2008, Uchiyama, et al.

* cited by examiner

*Primary Examiner* — Necholus Ogden, Jr.
(74) *Attorney, Agent, or Firm* — Oblon, Spivak, McClelland, Maier & Neustadt, L.L.P.

(57) ABSTRACT

Provided is a skin detergent composition containing a polyoxyethylene alkyl ether sulfate or an alkyl sulfate which composition is high in foam viscosity and creamy in foam quality. The skin detergent composition contains the following components (A), (B) and (C):

(A) a polyoxyethylene alkyl ether sulfate or an alkyl sulfate represented by a general formula (1):

$$R^1O(CH_2CH_2O)_nSO_3M \qquad (1);$$

(B) myristyl alcohol;
(C) one or more cationic polymers selected from the group consisting of the following (C-1) to (C-4): (C-1) a cationic group-containing copolymer obtained by a radical polymerization including as essential constituent monomers at least one nonionic group-containing vinyl monomer, at least one cationic group-containing vinyl monomer, and at least one crosslinkable vinyl monomer having in the molecule thereof at least two groups selected from a vinyl group, an acryloyl group, a methacryloyl group and an allyl group; (C-2) a cationized cellulose derivative; (C-3) a cationized guar gum derivative; and (C-4) a diallyl quaternary ammonium salt polymer or a diallyl quaternary ammonium salt/acrylamide copolymer, wherein the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 to 14% by weight.

12 Claims, No Drawings

SKIN CLEANSING COMPOSITION

FIELD OF THE INVENTION

The present invention relates to a skin detergent composition containing a polyoxyethylene alkyl ether sulfate or an alkyl sulfate, which is improved in foam quality.

BACKGROUND OF THE INVENTION

In detergent compositions, various surfactants are used according to the application purposes thereof, and many of such detergent compositions have a foam quality rough and lacking elasticity. Widely used detergent compositions containing polyoxyethylene alkyl ether sulfates or alkyl sulfates as basic components are excellent detergent compositions in the sense that such detergent compositions are excellent in foaming and are hardly affected by water quality; however, such detergent compositions are inferior in foam quality to detergent compositions including soaps as the fundamental ingredients thereof to bring about elastic and creamy foams having fine particle sizes. If such foam qualities, rough and lacking elasticity, of polyoxyethylene alkyl ether sulfates or alkyl sulfates can be improved into creamy foam qualities and detergent compositions excellent in storage stability can thereby be obtained, various formulations can be designed, and such formulations as detergent compositions are useful as body detergents for the skin preferring creamy foam quality.

In Patent Document 1, it is disclosed that a liquid detergent containing micellar-growth-promoting agents such as a non-soap anionic surfactant, an amphoteric surfactant, a nonionic surfactant having an HLB of 6 to 18 and a higher alcohol is excellent in detergency and satisfactory in low-temperature stability. In Patent Document 2, it is disclosed that a hair detergent containing a sulfate residue-containing anionic surfactant, a higher alcohol having 10 to 14 carbon atoms and a cationic polymer has a foam quality satisfactory in foaming and slippability at the time of cleansing the hair, has a smooth feeling at the time of rinsing the hair, and is excellent in feeling of use. In Patent Document 3, it is disclosed that a detergent composition containing an anionic surfactant, a specific nonionic surfactant and water and taking a gel or liquid crystalline form is highly viscous, satisfactory in resistance to sagging at the time of dealing with hand or a tool and nevertheless satisfactory in spreading performance, high in storage stability, and quick and satisfactory in foaming. In Patent Document 4, it is disclosed that a mild detergent composition containing an alkyl ethoxylated sulfate anionic surfactant, an amphoteric surfactant, an N-acylamino acid, a cationic cellulose ether derivative, water and a C12 to C14 fatty alcohol is excellent in thickening and foaming.

However, none of these detergent compositions is sufficiently satisfactory in the foam viscosity and foam quality improvement effects.

Patent Document 1: JP-A-2004-91522
Patent Document 2: JP-A-2003-212733
Patent Document 3: JP-A-2004-168951
Patent Document 4: U.S. Pat. No. 5,866,110

SUMMARY OF THE INVENTION

The present invention provides a skin detergent composition containing the following components (A), (B) and (C):

(A) a polyoxyethylene alkyl ether sulfate or an alkyl sulfate represented by a general formula (1):

$$R^1O(CH_2CH_2O)_nSO_3M \qquad (1)$$

wherein $R^1$ represents a straight chain or branched chain, alkyl or alkenyl group having 8 to 18 carbon atoms, an average addition number of moles n represents a number of 0 to 5, and M represents an alkali metal atom, an alkanolamine or ammonium;

(B) myristyl alcohol;

(C) one or more cationic polymers selected from the group consisting of the following (C-1) to (C-4):

(C-1) a cationic group-containing copolymer obtained by a radical polymerization including as essential constituent monomers at least one nonionic group-containing vinyl monomer represented by a general formula (I) or (II), at least one cationic group-containing vinyl monomer represented by a general formula (III) or (IV), and at least one crosslinkable vinyl monomer having in the molecule thereof at least two groups selected from a vinyl group, an acryloyl group, a methacryloyl group and an allyl group:

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

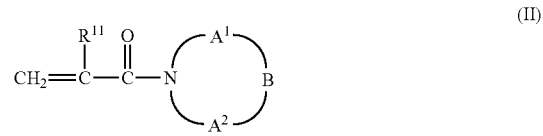

wherein $R^{11}$ represents the same meaning as above, $A^1$ and $A^2$ are the same or different and each represent a group represented by a formula $-(CH_2)_m-$ with the proviso that m represents an integer of 2 to 6, and B represents a group $-O-$ or $-CH_2-$,

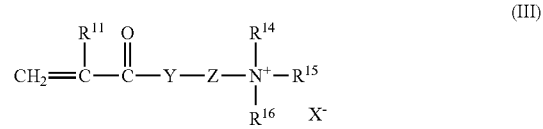

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group $-O-$, $-NH-$, $-CH_2-$ or $-O-CH_2CH(OH)-$, Z represents a straight chain or branched chain alkylene group having 1 to 4 carbon atoms with the proviso that this group has 0 to 3 carbon atoms when Y is $-CH_2-$, and $X^-$ represents a conjugate base of an acid, a halide ion or an alkyl sulfate group having 1 to 4 carbon atoms,

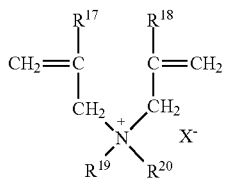

(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;

(C-2) a cationized cellulose derivative;

(C-3) a cationized guar gum derivative; and (C-4) a diallyl quaternary ammonium salt polymer or a diallyl quaternary ammonium salt/acrylamide copolymer, wherein the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 to 14% by weight.

Additionally, the present invention provides a method for producing a skin detergent composition containing the following components (A), (B) and (C):

(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more cationic polymers selected from the group consisting of the following (C-1) to (C-4):

(C-1) a cationic group-containing copolymer obtained by a radical polymerization including as essential constituent monomers at least one nonionic group-containing vinyl monomer represented by the general formula (I) or (II), at least one cationic group-containing vinyl monomer represented by the general formula (III) or (IV), and at least one crosslinkable vinyl monomer having in the molecule thereof at least two groups selected from a vinyl group, an acryloyl group, a methacryloyl group and an allyl group:

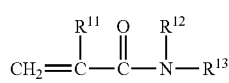

(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

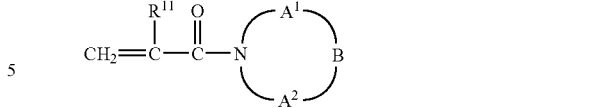

(II)

wherein $R^{11}$ represents the same meaning as above, $A^1$ and $A^2$ are the same or different and each represent a group represented by a formula —$(CH_2)_m$— with the proviso that m represents an integer of 2 to 6, and B represents a group —O— or —$CH_2$—,

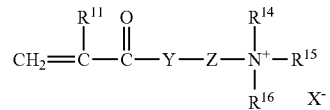

(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —$CH_2$— or —O—$CH_2CH(OH)$—, Z represents a straight chain or branched chain alkylene group having 1 to 4 carbon atoms with the proviso that this group has 0 to 3 carbon atoms when Y is —$CH_2$—, and $X^-$ represents a conjugate base of an acid, a halide ion or an alkyl sulfate group having 1 to 4 carbon atoms,

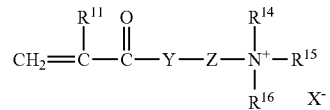

(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;

(C-2) a cationized cellulose derivative;

(C-3) a cationized guar gum derivative; and (C-4) a diallyl quaternary ammonium salt polymer or a diallyl quaternary ammonium salt/acrylamide copolymer, wherein the components (A), (B) and (C) are mixed together in such a way that the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 to 14% by weight.

Further, the present invention provides a method for cleansing the skin by using a composition containing the following components (A), (B) and (C):

(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more cationic polymers selected from the group consisting of the following (C-1) to (C-4):

(C-1) a cationic group-containing copolymer obtained by a radical polymerization including as essential constituent monomers at least one nonionic group-containing vinyl monomer represented by the general formula (I) or (II), at least one cationic group-containing vinyl monomer represented by the general formula (III) or (IV), and at least one crosslinkable vinyl monomer having in the molecule thereof at least two groups selected from a vinyl group, an acryloyl group, a methacryloyl group and an allyl group:

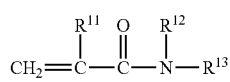
(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

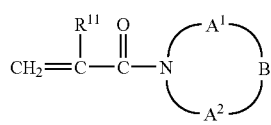
(II)

wherein $R^{11}$ represents the same meaning as above, $A^1$ and $A^2$ are the same or different and each represent a group represented by a formula —$(CH_2)_m$— with the proviso that m represents an integer of 2 to 6, and B represents a group —O— or —$CH_2$—,

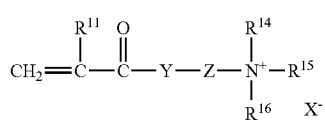
(III)

wherein $R^1$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —$CH_2$— or —O—$CH_2CH(OH)$—, Z represents a straight chain or branched chain alkylene group having 1 to 4 carbon atoms with the proviso that this group has 0 to 3 carbon atoms when Y is —$CH_2$—, and $X^-$ represents a conjugate base of an acid, a halide ion or an alkyl sulfate group having 1 to 4 carbon atoms,

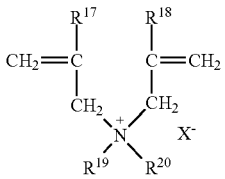
(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^{31}$ represents the same meaning as above;

(C-2) a cationized cellulose derivative;

(C-3) a cationized guar gum derivative; and (C-4) a diallyl quaternary ammonium salt polymer or a diallyl quaternary ammonium salt/acrylamide copolymer, wherein the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 to 14% by weight.

Yet further, the present invention provides a use of a composition containing the following components (A), (B) and (C) as a skin detergent:

(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more cationic polymers selected from the group consisting of the following (C-1) to (C-4):

(C-1) a cationic group-containing copolymer obtained by a radical polymerization including as essential constituent monomers at least one nonionic group-containing vinyl monomer represented by the general formula (I) or (II), at least one cationic group-containing vinyl monomer represented by the general formula (III) or (IV), and at least one crosslinkable vinyl monomer having in the molecule thereof at least two groups selected from a vinyl group, an acryloyl group, a methacryloyl group and an allyl group:

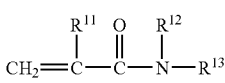
(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

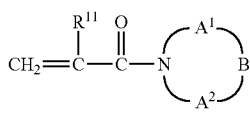
(II)

wherein $R^{11}$ represents the same meaning as above, $A^1$ and $A^2$ are the same or different and each represent a group represented by a formula —$(CH_2)_m$— with the proviso that m represents an integer of 2 to 6, and B represents a group —O— or —$CH_2$—,

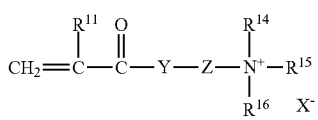
(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —$CH_2$— or —O—$CH_2CH(OH)$—, Z represents a straight chain or branched chain alkylene group having 1 to 4 carbon atoms with the proviso that this group has 0 to 3 carbon atoms when Y is —$CH_2$—, and $X^-$ represents a conjugate base of an acid, a halide ion or an alkyl sulfate group having 1 to 4 carbon atoms,

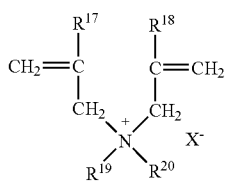
(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;
(C-2) a cationized cellulose derivative;
(C-3) a cationized guar gum derivative; and
(C-4) a diallyl quaternary ammonium salt polymer or a diallyl quaternary ammonium salt/acrylamide copolymer,
wherein the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 to 14% by weight.

DETAILED DESCRIPTION OF THE INVENTION

The present invention provides a skin detergent composition including a polyoxyethylene alkyl ether sulfate or an alkyl sulfate, the detergent composition being high in foam viscosity, creamy in foam quality.
The present inventors have found that by combining a polyoxyethylene alkyl ether sulfate or an alkyl sulfate with myristyl alcohol among higher alcohols and a specific cationic polymer, and further, by mixing these in a specific ratio, there can be obtained a skin detergent composition high in foam viscosity and creamy in foam quality.
The skin detergent composition of the present invention containing a polyoxyethylene alkyl ether sulfate or an alkyl sulfate is high in foam viscosity and creamy in foam quality.
Hereinafter, the present invention is described in more detail.
In the polyoxyethylene alkyl ether sulfate or the alkyl sulfate as the component (A), used in the present invention, represented by the above general formula (1), $R^1$ is a straight chain or branched chain, alkyl or alkenyl group having 8 to 18 carbon atoms; such a group preferably has 10 to 16 carbon atoms, more preferably 12 to 14 carbon atoms from the viewpoint of the detergency and foamability, and is preferably an alkyl group. Additionally, the alkyl group or the alkenyl group as $R^1$ may be of a straight chain or a branched chain, and is preferably of a straight chain. The average addition number of moles n represents a number of 0 to 5, and is preferably 1 to 3, more preferably 1 to 2 from the viewpoint of the detergency and foamability. M represents an alkali metal atom, an alkanolamine or ammonium; examples of the alkali metal include sodium and potassium, and preferable of these is sodium. Preferable as the alkanolamine is triethanolamine.
Preferable specific examples of the component (A) preferably include sodium polyoxyethylene (2) lauryl ether sulfate and ammonium polyoxyethylene (1) lauryl ether sulfate.
One or more types of the component (A) may be used. The content of the component (A) in the skin detergent composition is 5 to 70% by weight, preferably 10 to 70% by weight and more preferably 12 to 65% by weight in the whole composition from the viewpoint of the foamability and solution viscosity. When the skin detergent composition of the present invention is a composition such as a face wash, the content of the component (A) is preferably 30 to 70% by weight, more preferably 30 to 65% by weight and even more preferably 30 to 60% by weight in the detergent composition. Additionally, when the skin detergent composition of the present invention is a composition such as a liquid body detergent, the content of the component (A) is preferably 5 to 25% by weight, more preferably 6 to 25% by weight, more preferably 6 to 20% by weight and even more preferably 10 to 20% by weight in the detergent composition.
The component (B) used in the present invention is myristyl alcohol. According to the investigation of the present inventors, when the component (B) is combined with the component (A), among various higher alcohols, myristyl alcohol is particularly excellent in the effect of generating foam small in foam particle size, high in viscoelasticity and creamy. Specifically, the foam particle size is smaller when the component (A) is combined with myristyl alcohol than when combined with lauryl alcohol or palmityl alcohol, and the foam quality is creamy when combined with myristyl alcohol. Additionally, the viscoelasticity of the foam obtained when the component (A) is combined with myristyl alcohol is higher than that obtained when the component (A) is combined with lauryl alcohol or palmityl alcohol, and the foam is elastic when the component (A) is combined with myristyl alcohol.
The content the component (B) in the skin detergent of the present invention is more than 1 to 14% by weight, preferably 1.1 to 14% by weight, more preferably 1.1 to 10% by weight and even more preferably 1.2 to 10% by weight in the whole composition from the viewpoint of the foam quality improvement effect and foamability. When the skin detergent composition of the present invention is a composition such as a face wash, the content of the component (B) is preferably 2 to 14% by weight, more preferably 4 to 14% by weight and even more preferably 4 to 10% by weight in the detergent composition. Additionally, when the skin detergent composition of the present invention is a composition such as a liquid body detergent, the content of the component (B) is preferably more than 1 to 3% by weight, more preferably 1.1 to 2.5% by weight and even more preferably 1.2 to 2.5% by weight in the detergent composition.

Examples of the cationic polymers of the component (C) used in the present invention include one or more selected from the group consisting of the following (C-1) to (C-4):

(C-1) a cationic group-containing copolymer obtained by a radical polymerization including as essential constituent monomers at least one nonionic group-containing vinyl monomer represented by the general formula (I) or (II), at least one cationic group-containing vinyl monomer represented by the general formula (III) or (IV), and at least one crosslinkable vinyl monomer having in the molecule thereof at least two groups selected from a vinyl group, an acryloyl group, a methacryloyl group and an allyl group:

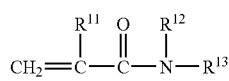

(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

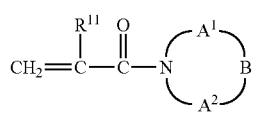

(II)

wherein $R^{11}$ represents the same meaning as above, $A^1$ and $A^2$ are the same or different and each represent a group represented by a formula $-(CH_2)_m-$ with the proviso that m represents an integer of 2 to 6, and B represents a group $-O-$ or $-CH_2-$,

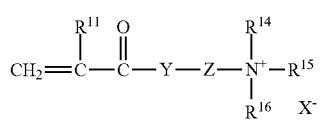

(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group $-O-$, $-NH-$, $-CH_2-$ or $-O-CH_2CH(OH)-$, Z represents a straight chain or branched chain alkylene group having 1 to 4 carbon atoms with the proviso that this group has 0 to 3 carbon atoms when Y is $-CH_2-$, and $X^-$ represents a conjugate base of an acid, a halide ion or an alkyl sulfate group having 1 to 4 carbon atoms,

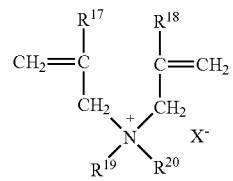

(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;

(C-2) a cationized cellulose derivative;
(C-3) a cationized guar gum derivative; and
(C-4) a diallyl quaternary ammonium salt polymer or a diallyl quaternary ammonium salt/acrylamide copolymer.

Hereinafter, the (C-1) cationic group-containing copolymer of the component (C) is described in detail.

(i) Nonionic Group-Containing Vinyl Monomers

Specific examples of the monomer represented by the general formula (1) include (meth)acrylamide, N-methyl(meth)acrylamide, N,N-dimethyl (meth)acrylamide, N,N-diethyl (meth)acrylamide, N-n-propyl(meth)acrylamide, N-isopropyl(meth)acrylamide, N-t-butyl(meth)acrylamide, N-isobutyl(meth)acrylamide and N-hydroxypropyl(meth)acrylamide. Examples of the monomer represented by the general formula (II) include N-(meth)acryloylmorphorine.

(ii) Cationic Group-Containing Vinyl Monomers

Specific examples of the monomer represented by the above general formula (III) include acid-neutralized products prepared by neutralizing the following compounds with an acid or quaternary ammonium salts prepared by quaternizing the following compounds with a quaternizing agent: dialkylamino group-containing (meth)acrylic acid esters or (meth)acrylamides such as dimethylaminoethyl (meth)acrylate, diethylaminoethyl (meth)acrylate, dipropylaminoethyl (meth)acrylate, diisopropylaminoethyl (meth)acrylate, dibutylaminoethyl (meth)acrylate, diisobutylaminoethyl (meth)acrylate, di-t-butylaminoethyl (meth)acrylate, dimethylaminopropyl(meth)acrylamide, diethylaminopropyl(meth)acrylamide, dipropylaminopropyl(meth)acrylamide, diisopropylaminopropyl(meth)acrylamide, dibutylaminopropyl(meth)acrylamide, diisobutylaminopropyl(meth)acrylamide, and di-t-butylaminopropyl(meth)acrylamide.

Specific examples of the monomer represented by the general formula (IV) include diallyl-type quaternary ammonium salts such as dimethyldiallylammonium chloride and diethyldiallylammonium chloride.

Examples of the acids suitable for preparing the above-mentioned acid-neutralized products include: inorganic acids such as hydrochloric acid, sulfuric acid, nitric acid and phosphoric acid; and organic acids having 1 to 22 carbon atoms in total such as acetic acid, formic acid, maleic acid, fumaric acid, citric acid, tartaric acid, adipic acid, sulfamic acid, toluenesulfonic acid, lactic acid, pyrrolidone-2-carboxylic acid, succinic acid, propionic acid and glycolic acid. Examples of the quaternizing agent suitable for preparing the above-mentioned quaternary ammonium salts include: alkyl halides having 1 to 8 carbon atoms such as methyl chloride, ethyl chloride, methyl bromide and methyl iodide; and common alkylation agents such as dimethyl sulfate, diethyl sulfate and di-n-propyl sulfate.

More preferable examples of the monomer represented by the above general formula (III) or (IV) include: quaternary ammonium salts prepared by quaternizing, with the above-mentioned quaternizing agents, dimethylaminoethyl (meth) acrylate, diethylaminoethyl (meth)acrylate, dimethylaminopropyl(meth)acrylamide or diethylaminopropyl(meth)acrylamide; or dimethyldiallylammonium chloride. The acid-neutralized product monomers undergo the dissociation of the acid used for neutralization depending on the pH and others of the system concerned to modify the polymer structure, and hence have a drawback such that the viscosity stability is low. Also from this viewpoint, quaternary ammonium salt-type monomers are more preferable.

(iii) Crosslinkable Vinyl Monomers

Examples of the crosslinkable vinyl monomer include: (meth)acrylates of polyhydric alcohols such as ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, 1,2-butylene glycol di(meth)acrylate, 1,3-butylene glycol di(meth)acrylate, neopentyl glycol di(meth)acrylate, glycerin di(meth)acrylate, glycerin tri(meth)acrylate, trimethylolpropane tri(meth)acrylate, and pentaerythritol tetra(meth)acrylate; acrylamides such as N-methylallylacrylamide, N-vinylacrylamide, N,N'-methylenebis(meth)acrylamide and bisacrylamide acetate; divinyl compounds such as divinylbenzene, divinyl ether and divinylethylene urea; polyallyl compounds such as diallyl phthalate, diallyl maleate, diallylamine, triallylamine, triallylammonium salt, allyl-etherified pentaerythritol, and allyl-etherified sucrose having in the molecule thereof at least two allyl ether units; and (meth)acrylates of unsaturated alcohols such as vinyl (meth)acrylate, allyl (meth)acrylate, and 2-hydroxy-3-acryloyloxypropyl (meth)acrylate.

Preferable among these crosslinkable monomers is ethylene glycol di(meth)acrylate, polyethylene glycol di(meth)acrylate, divinylbenzene, pentaerythritol triallyl ether or pentaerythritol tetraallyl ether.

(iv) Other Vinyl Monomers

The cationic group-containing copolymer of the component (A) can include, as the constituent components thereof, in addition to the above-mentioned three types of vinyl monomers as the essential constituent units, other vinyl monomers capable of copolymerizing with these essential vinyl monomers. Examples of the other vinyl monomers include (meth) acrylic acid derivatives such as methyl (meth)acrylate, ethyl (meth)acrylate, n-propyl (meth)acrylate, isopropyl (meth) acrylate, n-butyl (meth)acrylate, isobutyl (meth)acrylate, t-butyl (meth)acrylate, n-pentyl (meth)acrylate, neopentyl (meth)acrylate, cyclopentyl (meth)acrylate, n-hexyl (meth) acrylate, cyclohexyl (meth)acrylate, n-octyl (meth)acrylate, isooctyl (meth)acrylate, 2-ethylhexyl (meth)acrylate, n-decyl (meth)acrylate, isodecyl (meth)acrylate, lauryl (meth)acrylate, tridecyl (meth)acrylate, stearyl (meth)acrylate, isostearyl (meth)acrylate, behenyl (meth)acrylate, phenyl (meth) acrylate, toluoyl (meth)acrylate, xylyl (meth)acrylate, benzyl (meth)acrylate, 2-ethoxyethyl (meth)acrylate, 2-butoxy (meth)acrylate, 2-phenoxy (meth)acrylate, 3-methoxypropyl (meth)acrylate and 3-ethoxypropyl (meth)acrylate.

The above-mentioned other vinyl monomers each are preferably used in a proportion of 30% by weight or less and more preferably in a proportion of 15% by weight or less in the total amount of all the monomers constituting the cationic group-containing copolymer.

(v) Cationic Group-Containing Copolymer

The mixing ratio between the nonionic group-containing vinyl monomer ($a_1$) and the cationic group-containing vinyl monomer ($a_2$), both being the monomers to form the cationic group-containing copolymer, in terms of the molar ratio ($a_1$)/($a_2$), is preferably 2/98 to 98/2, and more preferably 40/60 to 97/3. When this molar ratio is large, the development of thixotropic behavior becomes easy, and when this molar ratio is small, the viscosity retention at low shear rate becomes easy; thus, for the purpose of developing both of these properties, the ($a_1$)/($a_2$) ratio preferably falls within the above-mentioned range.

The proportion of the crosslinkable vinyl monomer ($a_3$) is preferably 0.002 to 5% by weight, and more preferably 0.002% by weight or more and less than 0.1% by weight in relation to the total amount of all the monomers. When the proportion of the monomer ($a_3$) is 0.002% by weight or more, the viscosity of a hydrogel formed from the cationic group-containing copolymer is sufficient, and when the proportion of the monomer ($a_3$) is 5% by weight or less, the hydrogel exhibits soft feeling and satisfactory slippability.

Examples of a preferable embodiment of the (C-1) cationic group-containing copolymer of the component (C) of the present invention include the N,N-dimethylaminoethyl methacrylate diethyl sulfate/N,N-dimethylacrylamide/polyethylene glycol dimethacrylate copolymer represented by the following formula:

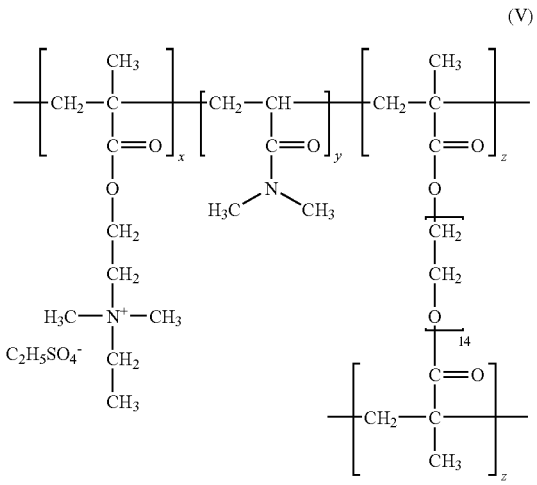

wherein, in terms of molar ratio, x/y=1/9 to 5/5, (x+Y+z)/z=1/0.1 to 1/0.002.

Commercially available examples of the cationic group-containing copolymer include Sofcare KG-301W (manufactured by Kao Corp.; x:y:z=30:70:0.0038 (molar ratio)), Sofcare KG-101E (manufactured by Kao Corp.; x:y:z=10:90:0.0035 (molar ratio)) and Sofcare KG-301P (manufactured by Kao Corp.; x:y:z=30:70:0.0038 (molar ratio)).

Hereinafter, the (C-2) cationized cellulose derivative of the component (C) is described in detail.

As the (C-2) cationized cellulose derivative, the compound represented by the following general formula (VI) is preferable:

wherein in formula (VI), A represents the residue of the anhydroglucose unit, a is an integer of 50 to 20000, and each $R^{21}$ represents a substituent represented by the following general formula (VII):

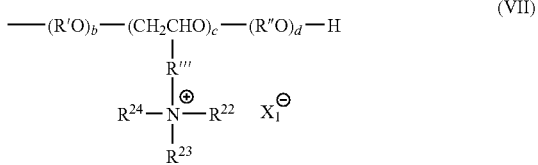

(VII)

wherein in formula (VII), R' and R" each represent an alkylene group having 2 or 3 carbon atoms, b represents an integer of 0 to 10, c represents an integer of 0 to 3, d represents an integer of 0 to 10, R''' represents an alkylene or hydroxyalkylene group having 1 to 3 carbon atoms, $R^{22}$, $R^{23}$ and $R^{24}$ are the same or different and each represent an alkyl, aryl or aralkyl group having up to 10 carbon atoms, or may form a heterocyclic ring including the nitrogen atom in the formula, and $X_1^-$ represents an anion (for example, a chloride, bromide, iodide, sulfate, sulfonate, methylsulfate, phosphate or nitrate ion).

The cation substitution degree of the cationized cellulose, namely, the average value of c per anhydroglucose unit is 0.01 to 1, and preferably 0.02 to 0.5. Additionally, the sum b+d is 1 to 3 on average. The substitution degree of 0.01 or less is not sufficient, and the substitution degree may be 1 or more; however, the substitution degree is preferably 1 or less from the viewpoint of the reaction yield. $R^{22}$, $R^{23}$ and $R^{24}$ are preferably, for example, such that these groups are all a $CH_3$ group, or two of them are short chain alkyl groups such as a $CH_3$ group and the remaining one of them is a long chain alkyl group having 10 to 20 carbon atoms. The molecular weight of the cationized cellulose to be used here is approximately between 100000 to 8000000.

Commercially available examples of the cationized cellulose include Poise C-60H (manufactured by Kao Corp.) and Poise C-80H (manufactured by Kao Corp.), and Polymer JR-400 (manufactured by Dow Chemical Co.)

Hereinafter, the (C-3) cationized guar gum derivative of the component (C) is described in detail.

As the (C-3) cationized guar gum derivative, the compound represented by the following general formula (VIII) is preferable:

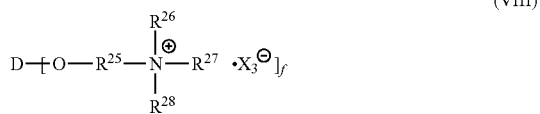

(VIII)

wherein D represents a guar gum residue, $R^{25}$ represents an alkylene or hydroxyalkylene group, $R^{26}$, $R^{27}$ and $R^{28}$ are the same or different and each represent an alkyl, aryl or aralkyl group having 10 or less carbon atoms, or may form a heterocyclic ring including the nitrogen atom in the formula, $X_3^-$ represents an anion (for example, a chloride, bromide, iodide, sulfate, sulfonate, methylsulfate, phosphate or nitrate ion), and f represents a positive integer.

The cation substitution degree of the cationized guar gum derivative is such that the cation group is introduced into the sugar unit preferably in a proportion of 0.01 to 1, and more preferably 0.02 to 0.5. Cationic polymers belonging to this type are described in Japanese Patent Publication Nos. 58-35640 and 60-46158, and JP-A-58-53996; commercially available examples of such cationic polymers include a product available under a trade name of Jaguar from Rhodia Inc., in particular, Jaguar C-13C, and additionally, Rabole gum CG-M manufactured by Dainippon Sumitomo Pharma Co., Ltd.

Hereinafter, the (C-4) diallyl quaternary ammonium salt polymer or diallyl quaternary ammonium salt/acrylamide copolymer of the component (C) is described in detail.

As the (C-4) diallyl quaternary ammonium salt polymer or diallyl quaternary ammonium salt/acrylamide copolymer, the compound represented by the following general formula (IX) or (X) is preferable:

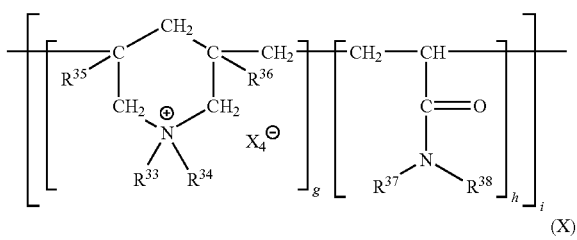

(IX)

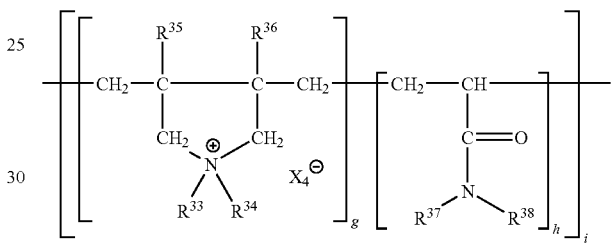

(X)

wherein in formulas (IX) and (X), $R^{33}$ and $R^{34}$ are the same or different, and each represent a hydrogen atom, an alkyl group having 1 to 18 carbon atoms, a phenyl group, an aryl group, a hydroxyalkyl group, an amidoalkyl group, a cyanoalkyl group, an alkoxyalkyl group or a carboalkoxyalkyl group, $R^{35}$, $R^{36}$, $R^{37}$ and $R^{38}$ are the same or different and each represent a hydrogen atom, a lower alkyl group having 1 to 3 carbon atoms or a phenyl group, $X_4^-$ represents an anion (for example, a chloride, bromide, iodide, sulfate, sulfonate, methylsulfate or nitrate ion), g represents an integer of 1 to 50, h represents an integer of 0 to 50, and i represents an integer of 150 to 8000.

The molecular weight of the diallyl quaternary ammonium salt/acrylamide copolymer is recommended to fall approximately within a range from 30000 to 2000000, and preferably from 100000 to 1000000.

Commercially available examples of such a copolymer include the products available under the trade name of Merquat from Nalco Co., in particular, Merquat 100, Merquat 550 and Merquat 3331.

One or more types of the component (C) may be used. The content of the component (C) in the skin detergent composition of the present invention is, from the viewpoint of the foam quality improvement effect and formability, preferably 0.05 to 5% by weight, more preferably 0.08 to 5% by weight and even more preferably 0.1 to 5% by weight in the whole composition. When the skin detergent composition of the present invention is a composition such as a face wash, the content of the component (C) is preferably 0.5 to 5% by weight, more preferably 0.8 to 5% by weight and even more preferably 1 to 5% by weight in the detergent composition. Additionally, when the skin detergent composition of the present invention is a composition such as a liquid body detergent, the content of the component (C) is preferably 0.05 to 2% by weight, more preferably 0.08 to 2% by weight and even more preferably 0.1 to 2% by weight in the detergent composition.

In the skin detergent composition of the present invention, the mixing ratios between the components (A), (B) and (C) are extremely important, from the viewpoint of the foam quality improvement effect and foamability.

The weight ratio of the component (A) to the component (B) is (A)/(B)=15/0.1 to 15/4, preferably 15/0.2 to 15/3 and more preferably 15/0.5 to 15/2 from the viewpoint of the foam quality improvement effect and foamability.

The weight ratio of the component (A) to the component (C) is (A)/(C)=15/0.05 to 15/3, preferably 15/0.08 to 15/2 and more preferably 15/0.1 to 15/1 from the viewpoint of the foam quality improvement effect and foamability.

The weight ratio of the component (B) to the component (C) is (B)/(C)=1/0.05 to 1/1, preferably 1/0.08 to 1/0.8 and more preferably 1/0.1 to 1/0.5 from the viewpoint of the foam quality improvement effect and foamability.

In the present invention, the foam viscosity is preferably 5000 mPa·s or more from the viewpoint of attaining creamy foam.

In the present invention, from the viewpoint of attaining creamy foam quality and high foam viscosity, the weight proportion of the component (A) in the whole surfactants is preferably 70% by weight or more.

The skin detergent composition of the present invention can be used as a skin detergent composition as it is, or as diluted with water. For example, the skin detergent composition of the present invention can be used as skin detergent compositions such as a face wash, a body shampoo, or a hand soap. In these skin detergent compositions, optional components may be mixed according to the purposes of the individual compositions. Examples of the optional components as referred to herein include anionic surfactants other than the component (A), nonionic surfactants, amphoteric surfactants and cationic surfactants, and conditioning components other than the component (B), usually mixed in these skin detergent compositions.

Examples of the anionic surfactants other than the component (A) include fatty acid salts, phosphoric acid ester salts, sulfosuccinic acid surfactants, polyoxyalkylenealkylamide ether sulfates, monoglyceride sulfates, olefinsulfonates, alkanesulfonates, acylated isethionates, acylated amino acid salts, polyoxyalkylenealkyl ether phosphates, and polyoxyalkylenealkyl ether acetates.

Examples of the nonionic surfactant include alkyl glycosides, alkyl polyglycosides, sucrose fatty acid esters, polyglycerin fatty acid esters, polyoxyalkylene alkyl ethers, fatty acid alkanol amides, alkyl amine oxides, and fatty acid esters of polyhydric alcohols. Preferable among these are fatty acid alkanol amides, alkyl glycosides and alkyl polyglycosides, and more preferable are alkyl glycosides and alkyl polyglycosides. Further, when the nonionic surfactant is an alkyl glycoside or an alkyl polyglycoside, such a compound brings about moderate grating feeling at the time of rising, and hence can suppress the sliminess inherent to a formulation including the component (A) so as to impart freshening feeling.

As an alkyl glycoside or an alkyl polyglycoside, a compound represented by the following general formula (5) is preferable:

$$R^9-O-(R^{10}O)_s-(G)_t \qquad (5)$$

wherein $R^9$ represents a straight chain or branched chain, alkyl, alkenyl or alkylphenyl group having 8 to 18 carbon atoms, $R^{10}$ represents an alkylene group having 2 to 4 carbon atoms, G represents a reducing sugar having 5 or 6 carbon atoms, an average addition number of moles s represents a number of 0 to 10, and the average sugar polymerization degree t represents a number of 1 to 10.

Among others, $R^9$ is preferably a straight chain or branched chain, alkyl or alkenyl group having 10 to 14 carbon atoms, the reducing sugar represented by G is preferably glucose, galactose or fructose, and more preferably glucose. The average sugar polymerization degree t is preferably 1 to 4. It is desirable to select the average sugar polymerization degree t in view of the physical properties derived from the alkyl or alkenyl group represented by $R^9$; for example, when $R^9$ is an alkyl group having 8 to 11 carbon atoms, it is preferable to select 1 to 1.4 for t, and when $R^9$ is an alkyl group having 12 to 14 carbon atoms,
it is preferable to select 1.5 to 4.0 for t. Specific examples of such an alkyl glycoside include decyl glucoside and lauryl glucoside.

One or more types of nonionic surfactants may be used. The content of a nonionic surfactant in the detergent composition of the present invention is, from the viewpoint of the foamability enhancement, preferably 0.01 to 20% by weight, more preferably 0.05 to 20% by weight and even more preferably 0.1 to 15% by weight in the whole composition.

Examples of the amphoteric surfactant include amidobetaine surfactants, amidoamino acid surfactants, carbobetaine surfactants, sulfobetaine surfactants, amidosulfobetaine surfactants, imidazolinium betaine surfactants and phosphobetaine surfactants. The content of each of these amphoteric surfactants is, from the viewpoint of the foamability, preferably 0.1 to 10% by weight, more preferably 0.1 to 5% by weight and even more preferably 0.5 to 5% by weight in the skin detergent composition of the present invention.

Examples of the cationic surfactant include quaternary ammonium salts represented by the following general formula (2):

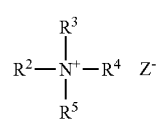

(2)

wherein at least one of $R^2$, $R^3$, $R^4$ and $R^5$ represents an alkoxy, alkenyloxy or alkanoylamino group having 8 to 28 carbon atoms in total, or an alkyl or alkenyl group optionally substituted with an alkenoylamino group, having 8 to 28 carbon atoms in total; each of the rest of these groups represents a benzyl group, an alkyl group having 1 to 5 carbon atoms, a hydroxyalkyl group or a polyoxyethylene group having a total addition number of moles of 10 or less, and $Z^-$ represents a halide ion or an organic anion.

Examples of the conditioning component include: higher alcohols such as lauryl alcohol, cetyl alcohol and stearyl alcohol; and oils such as silicone and silicone derivatives, lanolin, squalene, hydrocarbons, protein derivatives, and fatty acid esters of polyethylene glycol.

For example, the following other components commonly used can be mixed in the skin detergent composition of the present invention according to need within ranges that do not impair the advantageous effects of the present invention: water-soluble polymers such as polysaccharides including methyl cellulose, hydroxyethyl cellulose, carboxyvinyl polymer and xanthan gum; viscosity modifiers such as polyoxyalkylene sorbitan ester, polyoxyethylene glycol distearate and ethanol; chelating agents such as ethylenediaminetetraacetic acid (EDTA) and phosphonic acid salts; antiseptic agents such as methylparaben and butylparaben; effective components such as vitamins and the precursors thereof; animal and plant extracts and the derivatives thereof such as lecithin and gelatin; fine powders of polymers such as nylon and polyethylene; antiphlogistic agents such as dipotassium glycyrrhizinate; bactericides and antidandruff agents such as triclosan, trichlorocarban, octopirox and zinc pyrithione; antioxidant agents such as dibutylhydroxytoluene; pearling agents, ultraviolet absorbers; pH modifiers; colorants; perfumes; and water.

The skin detergent composition of the present invention can be produced by ordinary methods. For example, the skin detergent composition of the present invention can be produced by mixing, under stirring at temperatures ranging from 15 to 80° C., the components (A), (B) and (C), and other components according to need. The formulation of the skin detergent composition of the present invention is not particularly limited, but is optionally allowed to be any formulation of a liquid, a paste, a cream, a solid and a powder. Among these, a liquid, paste or cream formulation is preferable, and a liquid formulation is particularly preferable. When a liquid formulation is adopted, water is preferably used as a liquid medium.

EXAMPLES

Hereinafter, the present invention is described in more detail with reference to Examples.

Examples 1 to 15 and Comparative Examples 1 to 7

Preparation Method

Each of the skin detergents shown in Table 1 were prepared by mixing the components (B) and (C) in an aqueous solution of the component (A), and additionally other components according to need, and by heating the solution under stirring at 70° C. for 2 hours.

<Evaluation Methods>
(Foam Viscosity)

With 10 mL of 4° DH hard water, 1 mL of each of the body detergents thus prepared was diluted; and the diluted solution was foamed by a hand-washing operation for 20 seconds. The foam thus prepared was placed in a 50-mL beaker, and the foam viscosity (mPa·s) after 30 seconds at 25° C. was measured with a B-type viscometer (manufactured by Tokyo Keiki Co., Ltd.). In this measurement, the rotation number was 12 rpm, and a No. 3 rotor was used.

(Organoleptic Evaluation of Foam Quality)

With 10 mL of 4° DH hard water, 1 mL of each of the body detergents thus prepared was diluted; and the diluted solution was foamed by a hand-washing operation for 20 seconds. The foam thus prepared was subjected to an organoleptic evaluation. The organoleptic evaluation was conducted by a panel of 10 experts wherein the creaminess degree of the foam was graded in five ranks of from A to E. and averaged. A soap (15% aqueous solution of lauric acid/myristic acid/palmitic acid=6/4.5/4.5) was adopted as a standard and the foam was evaluated as follows: when the foam was extremely creamier than the foam of the soap, the foam quality was grades as "A"; when the foam was slightly creamier than the foam of the soap, the foam quality was grades as "B"; when the foam was comparable with the foam of the soap, the foam quality was grades as "C"; when the foam was slightly bubblier than the foam of the soap, the foam quality was grades as "D"; and when the foam was extremely bubblier than the foam of the soap, the foam quality was grades as "E."

<Evaluation Results>

As can be seen from the results shown in Table 1, in each of Comparative Examples 3 and 4 including only the components (A) and (C), the foam viscosity was low, and no foam quality improvement was able to be expected for these Comparative Examples. Comparative Examples 5 to 7 including the components (A) and (B), and a higher alcohol other than the component (C) or a fatty acid each exhibited a high foam viscosity, but were not able to exhibit drastically higher foam viscosities as compared to the skin detergents of the present invention (Examples 1 to 15) including the component (C).

TABLE 1

| | | Examples | | | | | | | |
|---|---|---|---|---|---|---|---|---|---|
| | Component (% by weight) | 1 | 2 | 3 | 4 | 5 | 6 | 7 | 8 |
| Component (A) | Sodium polyoxyethylene(2)lauryl ether sulfate[1) | 17.6 | 17.6 | 17.6 | 17.6 | 17.6 | 17.6 | 17.6 | 17.6 |
| Component (B) | Myristyl alcohol[2) | 1.2 | 1.2 | 1.2 | 1.2 | 1.2 | 1.2 | 1.2 | 1.2 |
| Component (C) | N,N-dimethylaminoethyl methacrylate diethyl sulfate/ N,N-dimethylacrylamide polyethylene glycol dimethacrylate copolymer (C-1)[3) | 0.25 | — | — | — | — | — | — | — |
| | N,N-dimethylaminoethyl methacrylate diethyl sulfate N,N-dimethylacrylamide polyethylene glycol dimethacrylate copolymer (C-1)[4) | — | 0.25 | — | — | — | 0.15 | 0.16 | — |
| | Acrylamide/acrylic acid/dimethyldiallylammonium chloride copolymer (C-4)[5) | — | — | 0.25 | — | — | — | 0.1 | 0.25 |
| | Cationized hydroxyethyl cellulose (C-2)[6) | — | — | — | 0.25 | — | 0.1 | — | — |
| | Cationized guar gum (C-3)[7) | — | — | — | — | 0.25 | — | — | — |
| | Decyl glucoside[8) | — | — | — | — | — | — | — | 2.0 |
| | Coconut oil fatty acid N-methyl-monoethanolamide[9) | — | — | — | — | — | — | — | — |
| | Lauric acid amide propylbetaine[10) | — | — | — | — | — | — | — | — |

TABLE 1-continued

| | | | | | | | | |
|---|---|---|---|---|---|---|---|---|
| Laurylhydroxysulfobetaine[11] | — | — | — | — | — | — | — | — |
| Stearyl alcohol[12] | — | — | — | — | — | — | — | — |
| Behenyl alcohol[13] | — | — | — | — | — | — | — | — |
| Ion-exchanged water | 80.95 | 80.95 | 80.95 | 80.95 | 80.95 | 80.95 | 80.94 | 78.95 |
| | | | | | | | | |
| Total | 100 | 100 | 100 | 100 | 100 | 100 | 100 | 100 |
| (A)/(B) | 15/1 | 15/1 | 15/1 | 15/1 | 15/1 | 15/1 | 15/1 | 15/1 |
| (A)/(C) | 15/0.2 | 15/0.2 | 15/0.2 | 15/0.2 | 15/0.2 | 15/0.2 | 15/0.2 | 15/0.2 |
| (B)/(C) | 1/0.21 | 1/0.21 | 1/0.21 | 1/0.21 | 1/0.21 | 1/0.21 | 1/0.22 | 1/0.21 |
| Foam viscosity (mPa·s) | 5630 | 12800 | 6250 | 8240 | 6200 | 6500 | 9500 | 8900 |
| Organoleptic evaluation of foam quality | B | A | B | A | B | B | A | A |

| | | | Examples | | | | | |
|---|---|---|---|---|---|---|---|---|
| | Component (% by weight) | 9 | 10 | 11 | 12 | 13 | 14 | 15 |
| Component (A) | Sodium polyoxyethylene(2)lauryl ether sulfate[1] | 17.6 | 17.6 | 17.6 | 17.6 | 17.6 | 17.6 | 17.6 |
| Component (B) | Myristyl alcohol[2] | 1.2 | 1.2 | 1.2 | 1.5 | 3.6 | 1.2 | 1.2 |
| Component (C) | N,N-dimethylaminoethyl methacrylate diethyl sulfate/ N,N-dimethylacrylamide polyethylene glycol dimethacrylate copolymer (C-1)[3] | — | — | — | — | — | — | — |
| | N,N-dimethylaminoethyl methacrylate diethyl sulfate N,N-dimethylacrylamide polyethylene glycol dimethacrylate copolymer (C-1)[4] | 0.25 | — | — | 0.25 | 0.25 | 0.08 | 1.00 |
| | Acrylamide/acrylic acid/dimethyldiallylammonium chloride copolymer (C-4)[5] | — | 0.25 | 0.25 | — | — | — | — |
| | Cationized hydroxyethyl cellulose (C-2)[6] | — | — | — | — | — | — | — |
| | Cationized guar gum (C-3)[7] | — | — | — | — | — | — | — |
| | Decyl glucoside[8] | — | — | — | — | — | — | — |
| | Coconut oil fatty acid N-methyl-monoethanolamide[9] | 1.5 | — | — | — | — | — | — |
| | Lauric acid amide propylbetaine[10] | — | 1.5 | — | — | — | — | — |
| | Laurylhydroxysulfobetaine[11] | — | — | 1.0 | — | — | — | — |
| | Stearyl alcohol[12] | — | — | — | — | — | — | — |
| | Behenyl alcohol[13] | — | — | — | — | — | — | — |
| | Ion-exchanged water | 79.45 | 79.45 | 79.95 | 80.65 | 78.55 | 81.12 | 80.20 |
| | | | | | | | | |
| | Total | 100 | 100 | 100 | 100 | 100 | 100 | 100 |
| | (A)/(B) | 15/1 | 15/1 | 15/1 | 15/1.3 | 15/3 | 15/1 | 15/1 |
| | (A)/(C) | 15/0.2 | 15/0.2 | 15/0.2 | 15/0.2 | 15/0.2 | 15/0.07 | 15/0.85 |
| | (B)/(C) | 1/0.21 | 1/0.21 | 1/0.21 | 1/0.17 | 1/0.07 | 1/0.08 | 1/0.83 |
| | Foam viscosity (mPa·s) | 17200 | 8200 | 7500 | 14500 | 8500 | 5700 | 18500 |
| | Organoleptic evaluation of foam quality | A | A | B | A | A | B | A |

| | | | Comparative Examples | | | | | |
|---|---|---|---|---|---|---|---|---|
| | Component (% by weight) | 1 | 2 | 3 | 4 | 5 | 6 | 7 |
| Component (A) | Sodium polyoxyethylene(2)lauryl ether sulfate[1] | 17.6 | 17.6 | 17.6 | 17.6 | 17.6 | 17.6 | 17.2 |
| Component (B) | Myristyl alcohol[2] | — | 1.2 | — | — | 1.2 | 1.2 | 2.0 |
| Component (C) | N,N-dimethylaminoethyl methacrylate diethyl sulfate/ N,N-dimethylacrylamide polyethylene glycol dimethacrylate copolymer (C-1)[3] | — | — | 0.25 | — | — | — | — |
| | N,N-dimethylaminoethyl methacrylate diethyl sulfate N,N-dimethylacrylamide polyethylene glycol dimethacrylate copolymer (C-1)[4] | — | — | — | — | — | — | — |
| | Acrylamide/acrylic acid/dimethyldiallylammonium chloride copolymer (C-4)[5] | — | — | — | — | — | — | — |
| | Cationized hydroxyethyl cellulose (C-2)[6] | — | — | — | 0.1 | — | — | — |
| | Cationized guar gum (C-3)[7] | — | — | — | — | — | — | — |
| | Decyl glucoside[8] | — | — | — | — | — | — | — |
| | Coconut oil fatty acid N-methyl-monoethanolamide[9] | — | — | — | — | — | — | — |
| | Lauric acid amide propylbetaine[10] | — | — | — | — | — | — | — |
| | Laurylhydroxysulfobetaine[11] | — | — | — | — | — | — | — |

TABLE 1-continued

|  |  |  |  |  |  |  |  |
|---|---|---|---|---|---|---|---|
| Stearyl alcohol[12] | — | — | — | — | 0.2 | — | 0.2 |
| Behenyl alcohol[13] | — | — | — | — | — | 0.2 | — |
| Ion-exchanged water | 82.4 | 81.2 | 82.15 | 82.3 | 81.0 | 81.0 | 80.6 |
| Total | 100 | 100 | 100 | 100 | 100 | 100 | 100 |
| (A)/(B) | — | 15/1 | — | — | 15/1 | 15/1 | 15/1.7 |
| (A)/(C) | — | — | 15/0.2 | 15/0.09 | — | — | — |
| (B)/(C) | — | — | — | — | — | — | — |
| Foam viscosity (mPa · s) | 500 | 3540 | 650 | 470 | 3440 | 2650 | 1990 |
| Organoleptic evaluation of foam quality | E | C | D | D | C | C | C |

[1] Emal 227; manufactured by Kao Corp.
[2] Kalcol 4098; manufactured by Kao Corp.
[3] Sofcare KG-101E; manufactured by Kao Corp.
[4] Sofcare KG-301P; manufactured by Kao Corp.
[5] Merquat Plus 3331; manufactured by Nalco Co.
[6] Poise C-60H; manufactured by Kao Corp.
[7] Rabole gum CG-M; manufactured by Dainippon Sumitomo Pharma Co., Ltd.
[8] Mydol 10; manufactured by Kao Corp.
[9] Aminon C-11S; manufactured by Kao Corp.
[10] Amphitol 20AB; manufactured by Kao Corp.
[11] Amphitol 20HD; manufactured by Kao Corp.
[12] Kalcol 8098; manufactured by Kao Corp.
[13] Kalcol 220-80; manufactured by Kao Corp.

Example 16

A body shampoo having the following composition was prepared.

| (Component) | (% by weight) |
|---|---|
| Sodium polyoxyethylene(2)lauryl ether sulfate (Emal 227; manufactured by Kao Corp.) | 15.0 |
| Myristyl alcohol (Kalcol 4098; manufactured by Kao Corp.) | 1.5 |
| Laurylhydroxysulfobetaine (Amphitol 20HD; manufactured by Kao Corp.) | 2.5 |
| Cationized cellulose (Poise C-60H; manufactured by Kao Corp.) | 0.1 |
| Sodium chloride | 0.5 |
| Perfume, Methylparaben | q.s. |
| Purified water | Balance |
| Total | 100.0 |

The body shampoo of Example 16 was abundant in the foam amount, and the entire body was able to be washed with comfortable creamy foam.

Example 17

A face wash having the following composition was prepared.

| (Component) | (% by weight) |
|---|---|
| Sodium polyoxyethylene(2)lauryl ether sulfate (Emal 227; manufactured by Kao Corp.) | 52.6 |
| Myristyl alcohol (Kalcol 4098; manufactured by Kao Corp.) | 5.1 |
| Laurylhydroxysulfobetaine (Amphitol 20HD; manufactured by Kao Corp.) | 8.0 |
| Glycerin | 1.0 |
| Sorbitol | 2.0 |
| N,N-dimethylaminoethyl methacrylate diethyl sulfate/N,N-dimethylacrylamide/polyethylene glycol dimethacrylate copolymer (Sofcare KG-301P; manufactured by Kao Corp.) | 0.6 |
| Perfume, Methylparaben | q.s |
| Purified water | Balance |
| Total | 100.0 |

The face wash of Example 17 was rich in foam quality and produced a large amount of fine foam, and the face was able to be washed mildly with creamy foam quality.

Example 18

A hand soap having the following composition was prepared.

| (Component) | (% by weight) |
|---|---|
| Sodium polyoxyethylene(2)lauryl ether sulfate (Emal 227; manufactured by Kao Corp.) | 18.5 |
| Lauryl alcohol (Kalcol 2098; manufactured by Kao Corp.) | 0.5 |
| Myristyl alcohol (Kalcol 4098; manufactured by Kao Corp.) | 1.8 |
| Laurylhydroxysulfobetaine (Amphitol 20HD; manufactured by Kao Corp.) | 2.9 |
| Cationized cellulose (Poise C-60H; manufactured by Kao Corp.) | 0.1 |
| N,N-dimethylaminoethyl methacrylate diethyl sulfate/N,N-dimethylacrylamide/polyethylene glycol dimethacrylate copolymer (Sofcare KG-301P; manufactured by Kao Corp.) | 0.2 |
| Perfume, Methylparaben | q.s. |
| Purified water | Balance |
| Total | 100.0 |

The hand soap of Example 18 was satisfactory in foamability so as to quickly bring about fine foam.

Example 19

A body shampoo having the following composition was prepared.

| (Component) | (% by weight) |
|---|---|
| Sodium polyoxyethylene(2)lauryl ether sulfate (Emal 227; manufactured by Kao Corp.) | 14.2 |
| Myristyl alcohol (Kalcol 4098; manufactured by Kao Corp.) | 1.8 |
| N-Methyl-monoethanolamide (Aminon C-11S; manufactured by Kao Corp.) | 2.0 |
| Laurylhydroxysulfobetaine (Amphitol 20HD; manufactured by Kao Corp.) | 1.0 |
| Decyl glucoside (Mydol 10; manufactured by Kao Corp.) | 2.0 |
| Dimethyldiallylammonium chloride/acrylamide copolymer (Merquat 550; manufactured by Nalco Co.) | 0.36 |
| Polyetylene glycol (Mw = 2500000) (Alcox E-100; manufactured by Meisei Chemical Co.) | 0.015 |
| Propylene glycol | 7.0 |
| Malic acid | 0.05 |
| Perfume, methylparaben | q.s. |
| Purified water | Balance |
| Total | 100.0 |

The body shampoo of Example 19 was excellent in initial foamability, brought about soft and fine foam, and made it possible to mildly cleanse the whole body.

Comparative Examples 8 to 11

The skin detergent compositions having the compositions shown in Table 2 were prepared and evaluated according to Examples 1 to 15 and Comparative Examples 1 to 7. The results thus obtained are shown in Table 2.

TABLE 2

| Component (% by weight) | Trade name | Effective component content (% by weight) | Com. Ex. 8 | Com. Ex. 9 | Com. Ex. 10 | Com. Ex. 11 |
|---|---|---|---|---|---|---|
| Coconut oil fatty acid amide propylbetaine | Amphitol 55AB | 30 | 5.15 | 5.15 | 5.15 | 5.15 |
| Sodium polyoxyethylene(2)lauryl ether sulfate | Emal 227 | 27 | 5.8 | 5.8 | 5.8 | 5.8 |
| Disodium lauryl POE(3)sulfosuccinate | Texapon SB-3 | 30 | 0.5 | 0.5 | 0.5 | 0.5 |
| Cationized hydroxyethyl cellulose | Poise C-80M | 100 | 0.1 | 0.1 | 0.1 | 0.1 |
| Polyoxyethylene sorbitan triisostearate (160E.O.) | Leodol TW-IS399C | 100 | 0.4 | 0.4 | 0.4 | 0.4 |
| Lauryl alcohol | Kalcol 2098 | 100 | — | 0.25 | 0.5 | 1 |
| Myristyl alcohol | Kalcol 4098 | 100 | — | 0.25 | 0.5 | 1 |
| Sodium sulfate | Sodium sulfate | 100 | 2.1 | — | — | — |
| Citric acid | Citric acid (50% aq.) | 50 | 0.1 | 0.1 | 0.1 | 0.1 |
| Methylparaben | Methylparaben | 100 | 0.3 | 0.3 | 0.3 | 0.3 |
| Perfume | Fleurs TRB0536 | 100 | 0.4 | 0.4 | 0.4 | 0.4 |
| Water | — |  | Balance | Balance | Balance | Balance |
| Foam viscosity (mPa · s) |  |  | 610 | 660 | 2410 | 3240 |

Texapon SB-3: manufactured by Cognis Co., Ltd.
Sodium sulfate: manufactured by Wako Pure Chem. Ind., Ltd.
Methylparaben: manufactured by Katayama Chem. Ind. Co., Ltd.
Citric acid: manufactured by Showa Kako Corp.
Other components: manufactured by Kao Corp.

As can be seen from the results shown in Table 2, the skin detergent compositions containing a small amount of the component (B) were low in foam viscosity, and no foam quality improvement was able to be expected for such skin detergent compositions.

What is claimed is:

1. A skin detergent composition comprising the following components (A), (B) and (C):
(A) a polyoxyethylene alkyl ether sulfate or an alkyl sulfate represented by a general formula (1):

$$R^1O(CH_2CH_2O)_nSO_3M \quad (1)$$

wherein $R^1$ represents a straight chain or branched chain, alkyl or alkenyl group having 8 to 18 carbon atoms, an average addition number of moles n represents a number of 0 to 5, and M represents an alkali metal atom, an alkanolamine or ammonium;
(B) myristyl alcohol;
(C) one or more cationic polymers selected from the group consisting of the following (C-1) to (C-4):
(C-1) a cationic group-containing copolymer obtained by a radical polymerization including as essential constituent monomers at least one nonionic group-containing vinyl monomer represented by a general formula (I) or (II), at least one cationic group-containing vinyl monomer represented by a general formula (III) or (IV), and at least one crosslinkable vinyl monomer having in the molecule thereof at least two groups selected from a vinyl group, an acryloyl group, a methacryloyl group and an allyl group:

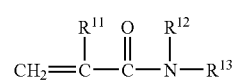
(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

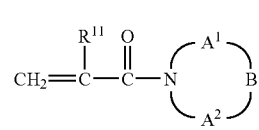
(II)

wherein $R^{11}$ represents the same meaning as above, $A^1$ and $A^2$ are the same or different and each represent a group represented by a formula —$(CH_2)_m$— with the proviso that m represents an integer of 2 to 6, and B represents a group —O— or —$CH_2$—,

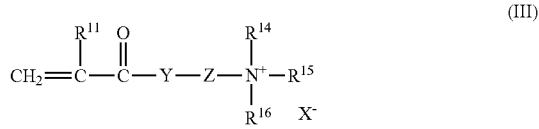

(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —CH$_2$— or —O—CH$_2$CH(OH)—, Z represents a straight chain or branched chain alkylene group having 1 to 4 carbon atoms with the proviso that this group has 0 to 3 carbon atoms when Y is —CH$_2$—, and X$^-$ represents a conjugate base of an acid, a halide ion or an alkyl sulfate group having 1 to 4 carbon atoms,

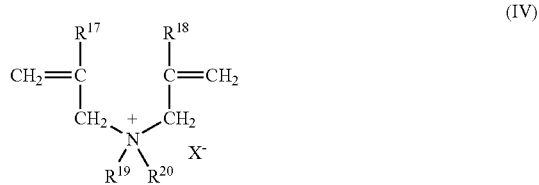

(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and X$^-$ represents the same meaning as above;
(C-2) a cationized cellulose derivative;
(C-3) a cationized guar gum derivative; and
(C-4) a diallyl quaternary ammonium salt polymer or a diallyl quaternary ammonium salt/acrylamide copolymer,
wherein the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 up to and including 14% by weight.

2. The skin detergent composition according to claim 1, wherein the foam viscosity is 5000 mPa·s or more.

3. The skin detergent composition according to claim 1, wherein the weight proportion of the component (A) in the whole surfactants is 70% by weight or more.

4. The skin detergent composition according to claim 1, wherein the (C) cationic polymer is (C-1).

5. The skin detergent composition according to claim 1, wherein the content of the component (A) is 5 to 70% by weight and the content of the component (C) is 0.05 to 5% by weight.

6. The skin detergent composition according to claim 1, wherein the content of the component (A) is 30 to 70% by weight, the content of the component (B) is 2 to 14% by weight and the content of the component (C) is 0.5 to 5% by weight.

7. The skin detergent composition according to claim 1, wherein the content of the component (A) is 5 to 25% by weight, the content of the component (B) is more than 1 up to and including 3% by weight and the content of the component (C) is 0.05 to 2% by weight.

8. The skin detergent composition according to claim 1, further comprising a nonionic surfactant.

9. The skin detergent composition according to claim 8, wherein the nonionic surfactant is one or more selected from an alkyl glycoside or an alkyl polyglycoside.

10. The skin detergent composition according to claim 1, further comprising an amphoteric surfactant.

11. A method for producing a skin detergent composition comprising the following components (A), (B) and (C):

(A) a polyoxyethylene alkyl ether sulfate or an alkyl sulfate represented by the general formula (1):

(1)

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;

(C) one or more cationic polymers selected from the group consisting of the following (C-1) to (C-4):

(C-1) a cationic group-containing copolymer obtained by a radical polymerization including as essential constituent monomers at least one nonionic group-containing vinyl monomer represented by the general formula (I) or (II), at least one cationic group-containing vinyl monomer represented by the general formula (III) or (IV), and at least one crosslinkable vinyl monomer having in the molecule thereof at least two groups selected from a vinyl group, an acryloyl group, a methacryloyl group and an allyl group:

(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

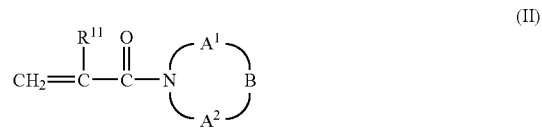

(II)

wherein $R^{11}$ represents the same meaning as above, $A^1$ and $A^2$ are the same or different and each represent a group represented by a formula —(CH$_2$)$_m$— with the proviso that m represents an integer of 2 to 6, and B represents a group —O— or —CH$_2$—,

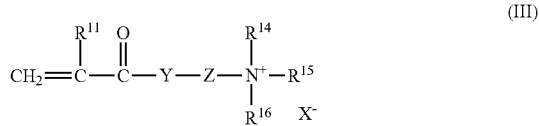
(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —CH$_2$— or —O—CH$_2$CH(OH)—, Z represents a straight chain or branched chain alkylene group having 1 to 4 carbon atoms with the proviso that this group has 0 to 3 carbon atoms when Y is —CH$_2$—, and $X^-$ represents a conjugate base of an acid, a halide ion or an alkyl sulfate group having 1 to 4 carbon atoms,

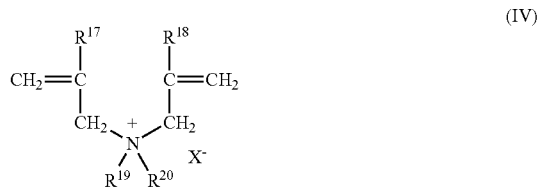
(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;

(C-2) a cationized cellulose derivative;
(C-3) a cationized guar gum derivative; and
(C-4) a diallyl quaternary ammonium salt polymer or a diallyl quaternary ammonium salt/acrylamide copolymer, comprising mixing the components (A), (B) and (C) together in such a way that the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)= 1/0.05 to 1/1, and the content of the component (B) is more than 1 up to and including 14% by weight.

12. A method comprising cleansing the skin by using a composition comprising the following components (A), (B) and (C):

(A) a polyoxyethylene alkyl ether sulfate or an alkyl sulfate represented by the general formula (1):

$$R^1O(CH_2CH_2O)_nSO_3M \quad (1)$$

wherein $R^1$ represents a straight chain or branched chain, alkyl or alkenyl group having 8 to 18 carbon atoms, the average addition number of moles n represents a number of 0 to 5, and M represents an alkali metal atom, an alkanolamine or ammonium;

(B) myristyl alcohol;
(C) one or more cationic polymers selected from the group consisting of the following (C-1) to (C-4):
(C-1) a cationic group-containing copolymer obtained by a radical polymerization including as essential constituent monomers at least one nonionic group-containing vinyl monomer represented by the general formula (I) or (II), at least one cationic group-containing vinyl monomer represented by the general formula (III) or (IV), and at least one crosslinkable vinyl monomer having in the molecule thereof at least two groups selected from a vinyl group, an acryloyl group, a methacryloyl group and an allyl group:

(I)

wherein $R^{11}$ represents a hydrogen atom or a methyl group, and $R^{12}$ and $R^{13}$ are the same or different and each represent a hydrogen atom or a straight chain or branched chain, alkyl or alkenyl group having 1 to 4 carbon atoms,

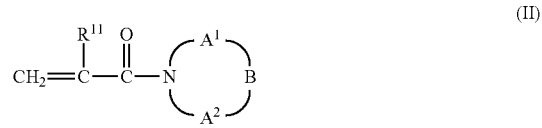
(II)

wherein $R^{11}$ represents the same meaning as above, $A^1$ and $A^2$ are the same or different and each represent a group represented by a formula —(CH$_2$)$_m$— with the proviso that m represents an integer of 2 to 6, and B represents a group —O— or —CH$_2$—,

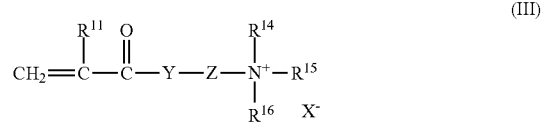
(III)

wherein $R^{11}$ represents the same meaning as above, $R^{14}$ and $R^{15}$ are the same or different and each represent an alkyl or alkenyl group having 1 to 4 carbon atoms, $R^{16}$ represents a hydrogen atom or an alkyl group having 1 to 4 carbon atoms, Y represents a group —O—, —NH—, —CH$_2$— or —O—CH$_2$CH(OH)—, Z represents a straight chain or branched chain alkylene group having 1 to 4 carbon atoms with the proviso that this group has 0 to 3 carbon atoms when Y is —CH$_2$—, and $X^-$ represents a conjugate base of an acid, a halide ion or an alkyl sulfate group having 1 to 4 carbon atoms,

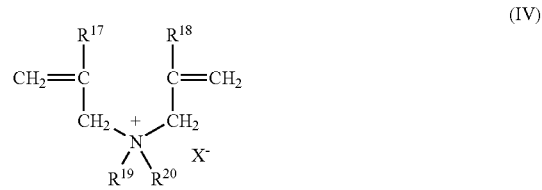
(IV)

wherein $R^{17}$ and $R^{18}$ are the same or different and each represent a hydrogen atom or a methyl group, $R^{19}$ and $R^{20}$ are the same or different and each represent a hydrogen atom or an alkyl group having 1 to 4 carbon atoms, and $X^-$ represents the same meaning as above;

(C-2) a cationized cellulose derivative;

(C-3) a cationized guar gum derivative; and (C-4) a diallyl quaternary ammonium salt polymer or a diallyl quaternary ammonium salt/acrylamide copolymer, wherein the weight ratio of the component (A) to the component (B) is (A)/(B)=15/0.1 to 15/4, the weight ratio of the component (A) to the component (C) is (A)/(C)=15/0.05 to 15/3, the weight ratio of the component (B) to the component (C) is (B)/(C)=1/0.05 to 1/1, and the content of the component (B) is more than 1 up to and including 14% by weight.

* * * * *